United States Patent [19]

Wunderlich et al.

[11] Patent Number: 5,401,502
[45] Date of Patent: Mar. 28, 1995

[54] PELLETS CONTAINING PLANT EXTRACTS, PROCESS OF MAKING SAME AND THEIR PHARMACEUTICAL PERORAL OR COSMETIC USE

[75] Inventors: Jens-Christian Wunderlich, Heidelberg; Ursula Schick, Wiesloch; Jurgen Freidenreich, Schriesheim; Jurgen Werry, Ludwigshafen, all of Germany

[73] Assignee: ALFATEC Pharma GmbH, Heidelberg, Germany

[21] Appl. No.: 876,866

[22] Filed: Apr. 30, 1992

[30] Foreign Application Priority Data

Jan. 17, 1992 [DE] Germany .................. 42 01 179.5

[51] Int. Cl.⁶ .................. A01N 65/00; A61K 9/48
[52] U.S. Cl. .................. 424/195.1; 424/451; 424/464; 424/456; 424/484; 424/485; 424/486; 424/487; 424/488; 424/492; 424/520
[58] Field of Search .................. 424/195.1, 520, 401, 424/408, 456, 484, 485, 486, 487, 488, 492, 464, 451

[56] References Cited

U.S. PATENT DOCUMENTS

| | | | |
|---|---|---|---|
| 3,691,281 | 9/1972 | Battista | 424/195.1 |
| 4,446,131 | 5/1984 | Maughan | 424/195.1 |
| 4,470,202 | 9/1984 | Buxton et al. | 34/5 |
| 4,500,510 | 2/1985 | Goldstein | 424/195.1 |
| 4,895,724 | 1/1990 | Cardinal et al. | 424/94.1 |
| 4,994,265 | 2/1991 | White | 424/195.1 |
| 5,019,400 | 5/1991 | Gombotz et al. | 424/497 |
| 5,089,407 | 2/1992 | Baker et al. | 435/179 |
| 5,254,294 | 10/1993 | Wunderlich et al. | 264/4 |

FOREIGN PATENT DOCUMENTS

| | | |
|---|---|---|
| 0362582 | 9/1989 | European Pat. Off. . |
| 6907579 | 11/1970 | Netherlands ............. 424/195.1 |

*Primary Examiner*—Thurman K. Page
*Assistant Examiner*—Peter F. Kulkosky
*Attorney, Agent, or Firm*—Omri M. Behr; Matthew J. McDonald

[57] ABSTRACT

Plant extract containing pellets are formed by a dispersion of plant extract or extracts in a matrix, principally comprising a skeleton builder namely collagen, gelatin, fractionated gelatin, a collagen hydrolysate, gelatin derivative plant proteins, or plant protein hydrolysates. They are shelf stable and their pharmacological as well as cosmetic properties are substantially unchanged in comparison to the native extracts. They may be produced by a simple process in which a solution of the skeleton former is mixed with liquid plant extract or emulsified with solid extracts, dissolved or suspended, the dispersion of the skeleton former and the plant extract dropped into a very cold inert fluid, suitably liquid nitrogen, to form the pellets and the thus formed pellets dried.

28 Claims, 1 Drawing Sheet

PELLETS CONTAINING PLANT EXTRACTS, PROCESS OF MAKING SAME AND THEIR PHARMACEUTICAL PERORAL OR COSMETIC USE

FIELD OF THE INVENTION

The present invention concerns pellets, that is to say, spheres containing plant extract or extracts characterized thereby that the plant extract dispersed in a matrix which principly consists of a skeleton which is a hydrophilic macromolecule.

The invention is further concerned with a protective process for the preparation of such pellets or solid spheres, which may be utilized for pharmaceutical, oral, or cosmetic purposes.

BACKGROUND OF THE INVENTION

Plant extracts as utilized in the present invention are plant juices directly obtained from the fresh plants, juices pressed out of fresh plants both in their original concentration, as well as, in concentrated form, filtered and unfiltered, hydrophilic (aqueous or alcoholic for example ethanol or 1,2-propylene glycol) extracts, as for example, homeopathic prototinctures, fluid extracts, macerates, lipophilic extracts (for example, garlic oil), etheric oils, total extracts or special standardized extracts (for example, having a particular content of flavoneglycocides) etheric oil extracts, individually isolated plant content materials (for example, rutin) synthetic analogs (such as, perfume oils, camphor, thymol, vanillin) and derivatized plant content materials (such as, aglyca).

In the individual cases dry extracts can also be used for example when the dry extract is again dissolved in the appropriate solvent, or decoctions produced therefrom. Furthermore, pulverized drug precursor materials for example, leaves, roots, herbs, etc. may thus be processed.

Plant extracts are natural products which in many cases are sensitive to outside influences such as light, oxidation by atmospheric oxygen, warmth, pH influences in solutions, or microbial attack. It is well known that for many active plant materials the optimal activity can only be obtained from fresh juices obtained from the plant or parts thereof (i.e. echinacea, pressed juice or aloe vera juice). Every procedure for conservation such as drying with heat, chemical conservation, heat treatment for conservation and the like influence the sensitive plant content material with respect to its chemical structure and thus, its activity. In most cases where fresh plant juices are involved, conservation against microbial attack is unavoidable in order to obtain at least a modest shelf life.

Furthermore, it should be realized that the dry content of such fresh plant juices is very small and it is necessary to transport or store large quantities of water.

Oxidation sensitive lipophilic plant extracts such as Vitamin E or garlic oil are exceedingly difficult to store in an unaltered form and must therefore be processed immediately. Etheric oils are very volatile and are difficult to handle in the fluid state. The task of the present invention therefore is to provide preservative free, shelf stable, concentrated, solid or semi-solid forms of plant extracts which can be readily redissolved and whose pharmacological or cosmetic properties, in comparison to the native plant juices remain unchanged.

SUMMARY OF THE INVENTION

This task is solved by the present Invention by producing plant extract containing pellets characterized by a dispersion of plant extracts in a matrix whose skeleton principally consists of a hydrophilic macromolecule.

As hydrophilic macromolecules there may be utilized collagen, gelatins, fractionated gelatins, collagen hydrolysates, gelatin derivatives, plant proteins, plant protein hydrolysates, elastin hydrolysates, as well as mixtures of the above named materials.

The task is further solved by a process for the preparation of such plant extract containing pellets characterized thereby that the skeleton forming material in solid or dissolved form is mixed with or emulsified with, for example, solid extract in a solution of the skeleton former, or suspended and formed into molded particles. The molded particles may, if necessary, be dried. Care should be taken however that no incompatibilities of the matrix system or the active materials are allowed to occur.

In particular, the present invention makes available molfed particles containing plant extract characterized by a dispersion of the plant extract in a matrix which comprises principally a skeleton former of a hydrophilic macromolecule selected from the group consisting of collagen, gelatins, fractionated gelatins, collagen hydrolysates, gelatin derivatives, elastin hydrolysates, plant proteins, plant protein hydrolysates and mixtures thereof.

Furthermore, the present invention makes available a process for the formation of plant extract containing molded particles characterized thereby that a) a skeleton former of hydrophilic macromolecules selected from the group consisting of collagen, gelatin, fractionated gelatins, collagen hydrolysates, gelatin derivatives, elastin hydrolysates, plant proteins, plant protein hydrolysates and mixtures thereof are mixed with the plant extracts which are selected from the group consisting of hydrophilic fluid plant extracts, aqueous extracts, alcoholic extracts, and mixtures thereof and b) the thus obtained mixture of skeleton former and plant extract is dropped into an exceedingly cold inert fluid to form molded body particles.

The preferred embodiments of the invention are described and claimed hereinbelow.

Plants extracts and the extracts obtained therefrom or individual components can for example, be flavonoids and their aglyca;

rutin, quercitin, diosmin, hyperocyde, (neo)hesperidin, hesperitine, ginko biloba (for example, ginkoflavono glycoside) crataegus extract (for example oligomeric procyanidine) buck wheats (for example, rutin) sophora japonica (for example, rutin), birch leaves (quercitin glycoside, hyperoside and rutin) elder blossoms (for example, rutin) linen blossoms (etheric oils with quercitin and farnesol) St. Johns wort oil (for example, olive oil extracts) calendula, arnica (for example oily extracts of blossoms with etheric oils, polar extracts with flavonoid lemon balm (for example flavone and etheric oils).

Etheric oils, sage (for example etheric oils with thymol) niseseed (etheric oils with trans-anethol), carnation oil (for example etheric oil with eugenol), camomile (camazulene, alpha-bisabolol, myrtols, (limonine, alpha-pinene, cineol), peppermint oil (for example, oil with menthol) caraway seed (for example, oil with carvone) larch (for example oil with alpha-pinene) Juniper, rosemarin, eucalyptus oil, lavender, fir needle oil, bergamo oil, citrus oil, lemon balm, marjoram, thyme, basil (stomatica or herbs) and fennel.

Fatty oils: for example, wheat germ oil and the vitamin E isolated therefrom, primrose oil (for example, gammalinolenic acid), plant lecithin (for example, soya lecithin) and sphingolipides and ceramides isolated from plants.

Immuno stimulants: echinacea purpuria (alcoholic extracts, fresh plant juice, pressed juice), elutheriococcus genticosus.

Alkaloids: rauwolfia, (for example, prajmaline evergreen, (for example vincamine).

Further phytopharmaceuticals: aloe, horse chestnuts (for example aescin), garlic (for example, garlic oil), pineapple (for example, bromelaein) ginseng (for example, ginsenoside), marythistle fruit (for example, extracts standardized on silbmarin), mouse thorn root (for example ruscogenine), valeriana (for example valepotriate, and tincture valerainae nigh), Kava Kava (for example Cavalactone), hop blossom (hop bitters), extract of passiflorae, gentian (for example ethanol extract), anthraquinone containing drug extracts, (for example, aloin containing aloe vera juice), pollen extract, algin extract, liquorice extract, palm extract, galphimia (for example, prototincture), mistletoe, (for example, aqueous ethanol extract), phytosterols (for example, beta-sitosterine), verbascom (aqueous alcohol extract), droseria (liquor wine extract), sandthorn fruit, (for example the juice thereof), marshmallow root, primula root extract, fresh plant extracts of mellow, comfrey, ivy, Schachtelhalm, Yarrpwe, ribwart (for exa,ple pressed juice) nettles, celandine, parsley.

Generally speaking, the plant extract is selected from the group consisting of solid plant extracts, liquid plant extracts, hydrophilic plant extracts, lipophilic plant extracts, individual plant content materials, as well as mixtures thereof.

The pellets of the present invention comprise round, unitary molded particles, having a diameter in the range of 0.8 to 2 mm. Furthermore, in accordance with the present invention, sizes of both 0.2 to 0.8, as well as 2 to 12 mm. may be produced. Pellets having at least a diameter of 2 mm., with respect to the present invention, are referred to solid spheres and are suitable as single unit dosage forms.

Surprisingly, these pellets have a high stability against abrasion (friability). They are shelf stable, readily dosable, and because of their special mode of production, have the properties of a free-flowing material. They can contain plant extracts, calculated as solid material content, concentrations of between 0.1 to 98 wt. %, suitably from 0.1 to 60 wt. %.

Surprisingly, it has been found that neither the type nor the composition of the content materials of the native plant content materials are altered by the pellets of the present invention. The process of the present invention being a cooling process, is a highly protective form of processing. The pellets containing the plant extracts can also be produced as lyophilisates or solid or gel formed pellets, depending on the mode of production.

Because of the transformation into pellet form with the matrix system of the present invention, the use of preservatives or heat treatment for preservation become superfluous.

A pelleted fresh plant juice is shelf stable. For example, where previously solvent extraction was necessary on grounds of stability, this can now be avoided.

Furthermore, transition of the fluids into the solid phase is possible (etheric oils, or fatty oils). This improves the shelf stability, transportability and handling of such materials.

The conventionally dried pellets of the present invention with or without softening additives, can be readily recognized by their characteristic, unchanging appearance; they are transparent or opaque and shiny.

The product of the present invention may be directly utilized, either for pharmaceutical purposes (i.e., internal utilization) or for cosmetic purposes.

For pharmaceutical purposes, the pellets may be processed as multiple unit dosage forms, as granulates in bags or in hard gelatin capsules. Furthermore, as potable granulates for the formation of potable solutions (instant teas), as well as single unit dosage forms, that is to say, single dosage pellets, for example, provided in suitable containers, blister or dosage dispensers constructed for single provision. A further single dose form can be made from freeze-dried pellets pressed into tablets which dissolve rapidly.

For cosmetic purposes, it is a particularly advantageous embodiment of the invention to utilize plant proteins or their hydrolysates, soluble collagen, gelatins, collagen hydrolysates, elastin or elastin hydrolysates as carrier materials for the molded particles.

Gelatin is a scleroprotein obtained from collagen containing material which has different properties, depending on the mode of production. It comprises basically four molecular weight fractions which influence the physicochemical properties thereof in dependence upon molecular weight and proportion by weight. The higher, for example, the portion of microgel ($10^7$ to $10^8$D) the higher is also the viscosity of the aqueous solution. Commercial materials contain up to 15 wt. % thereof. The fractions of alpha gelatin and its oligomers ($9.5 \times 10^4/10^5$ through $10^6$D) are determinative for gel solidity and generally lie between 10 and 40 wt. %. Molecular weights below alpha gelatins are designated as peptides and can, in commercially available gelatin qualities (below bloom numbers) comprise up to 80 wt. %.

Gelatin possesses a temperature-and concentration dependent sol/gel transition relationship, which is dependent upon the molecular composition. As the conventional method for designating the gel forming content, the bloom number is indicated. Low commercial qualities begin at 50 bloom and high bloom types register about 300 bloom.

Fractionated gelatins are a special type of gelatins and are obtained through special production techniques, for example ultrafiltration, from commercially available gelatin. The composition can be changed, for example by removal of peptides (molecular weight less than $9.5 \times 10^4$D) or by mixtures of individual fractions as, for example, alpha chains, dimers and trimers or microgel.

Collagen in native form is water insoluble. Through special production procedures, it is now possible to obtain soluble collagen types.

Gelatin derivatives are chemically altered gelatins, for example, succinylated gelatin, which can be utilized as a plasma expander.

By collagen hydrolysate is understood a product without gel forming quantities obtained from collagen or gelatin, by high pressure hydrolysis or enzymatic action. The molecular composition can, depending on the mode of production, lie between 100D up to less than $9.5 \times 10^4$D. Collagen hydrolysates are cold water soluble.

These materials of biogenic source are indicated for topical use, not only in view of excellent skin compatibility but they are also excellently compoundable in ointments, creams, and emulsions. Therein they show their particular quality, namely to operate to a certain extent as a emulsifiers and as emulsion stabilizers. Thus, for example, the addition of large amounts of skin irritating tensides can be further reduced which is helpful to the skin compatibility of pharmaceutical compositions, for example, those for the treatment of wounds or modern cosmetics. Gelatin and collagen hydrolysates are pharmaceutically acceptable inactive ingredients which may also be preferentially utilized in the cosmetic industry.

As newly developed products, there may be utilized plant proteins and the hydrolysates which correspond, in their properties, to a substantial extent with collagen hydrolysates. These are preferably obtained from wheat and soya and have, for example, molecular weights of between 200,000 to 300,000D and 1,000 to 120,000D respectively.

In utilizing plant proteins, plant protein hydrolysates, suitably collagen hydrolysates (cold water soluble gelatins) or gelatins with maximum molecular weight distribution of a few hundred D to below $10^5$D, the lyophilized carrier material of the molded particles of the present invention surprisingly form a highly porous network with stable mechanical properties.

The rapid solution of the above described pellet prescriptions is advantageous for instantaneous usage, for example, instant teas, instant juices (for example cough syrup) or preservative-free instant creams.

The improvement of the well known healing properties of, fresh plant juices for internal utilization (health care) can be advantageously achieved by the pellets of the present invention, in the form a preservative-free instant preparation. For example, if a fresh plant juice is cryopelleted with a rapidly dissolving matrix, there are obtained shelf stable pellets (which can be stored in bags) which can be totally dissolved in water, fruit juice, milk, or other drinks, within a few seconds. It is advantageous that complete ready-made drinks can also be produced hereby, consisting of fresh plant juices, a matrix of proteins of biogenic origin (for example collagen hydrolysates, wheat proteins) and natural skeleton formers, fruit juice extract, honey and other natural components. Components of the matrix such as, for example, gelatin, can mask undesirable tastes and glycerol and sorbitol can serve as tooth-friendly sweetening materials.

Where the pellets of the present invention are provided in non-lyophilized form, that is to say, in solid or half-solid form, they may advantageously be constructed of sol/gel forming hydrophilic molecules, for example, gelatin or fractionated gelatin, having a maximum molecular weight distribution of more than $10^5$D, wherein the consistency is in direct dependence upon the type and concentration of the softening additive.

Such softener containing pellets are exceedingly suitable for the conversion of etheric oils into solid and thus readily utilizable form.

In particular, semi-solid patents can be so introduced into the matrix mass that after application they melt or are dissolved. For external use as well as in the pharmaceutical area, the skin friendly action of the matrix made of natural materials, is therefore advantageous.

Hereinbelow the process for the preparation of the pellets of the present invention will be described in greater detail.

Further embodiments of the present invention are set forth in the United States application for Letters Patent as set forth herein, whose disclosure is incorporated herein by reference. These parallel U.S. applications have been filed in the United States Patent and Trademark Office by the same inventors on the same day and are as follows:

Title: "Aloe Vera Juice Containing Pellets for Production Thereof and the Use Thereof as Pharmaceutical Cosmetic and Peroral Agents", U.S. Ser. No. 07/876,876.

Title: "Pellets Containing Peptides, Method of Making Same and Use Thereof", U.S. Ser. No. 07/876,865.

Title: "Means for Containing Active Substances Having a Shell of Hydrophilic Macromolecules, Active Substances and Process for Preparation Thereof", U.S. Ser. No. 07/876,864.

Title: "Soft Gelatin Capsules", U.S. Ser. No. 07/876,863.

Title: "Peroral Dosage Form for Peptide Containing Medicaments, in Particular Insulin", U.S. Ser. No. 07/876,867.

Title: "Pellets Containing Dihydropyridine Derivatives Process for Production Thereof and Use as Rapid Action Dosage in Heart and Circulatory Diseases", U.S. Ser. No. 07/876,877.

Where there is employed an aqueous alcoholic or aqueous/alcoholic extract the process of production of plant extract containing pellets can be described in the following two-step process.

A) skeleton former in solid or dissolved form comprising hydrophilic molecules selected from the group consisting of gelatin, fractionated gelatin, collagen hydrolysate, gelatin derivatives, as well as mixtures thereof, is mixed with liquid, hydrophilic (aqueous, alcoholic, or water/alcoholic) plant extract.

B) The thus obtained mixture of skeleton former and fluid hydrophilic plant extract is then added dropwise to a very cold inert fluid thus forming the molded body.

The term molded body as utilized in the present invention, is directed to materials selected from the group consisting of powders, granulates, pellets, and aggregates which have substantially symmetrical dimensions.

In the description of the invention, the properties, production, and use of round pellets will preferentially be described.

It is understood that those skilled in the art could also advantageously use other molded particles selected from the group consisting of powders and granulates in substantially symmetrically formed aggregates for the formation o, suitably pharmaceutical dosage forms.

When there is utilized as the skeleton former, for example, cold water soluble collagen and/or plant protein hydrolysate, it is possible to operate in the gentlest manner, that is to say, without any use of heat.

In an embodiment described in the process step described under (A), there is provided a mass capable of forming drops principally consisting of hydrophilic macromolecules as skeleton formers, in particular plant proteins, plant protein hydrolysates, collagen, gelating, fractionated gelatin, collagen hydrolysates, elastin hydrolysates or gelatin derivatives, and aqueous, alcoholic, or aqueous/alcoholic plant extract.

Subsequently one can dissolve in the freshly obtained or already concentrated fluid aqueous, alcoholic, or aqueous alcoholic plant extract, the desired skeleton builder, in particular, plant protein, plant protein hydrolysate, collagen, gelatin, fractionated gelatin, gelatin derivative or collagen hydrolysate, or one can mix these in already dissolved form with the plant extract, wherein the type and amount of the added skeleton former and similarly the addition of further inactive ingredients, depend upon the ultimate utilization of the pellets. The concentration of the carrier material can be between 0.5 to 60% w/w, suitably between 0.5 and 30% (relative to the total mass to be worked). It is acceptable to raise the temperature into the range of between 30° C. and 45° C. during the addition gelatin in order to convert this into the sol form.

There may further be utilized additives selected from the group consisting of albumin, agar agar, gum arabic, pectin, tragacanth, xanthane, natural as well as modified starches, dextrans, dextrins, maltodextrin, chitosan, alginates, cellulose derivatives, polyvinyl pyrrolidone, dextran, sugar, glycine, lactose, mannitol, polyacrylic acid, polymers of methacrylic acid, polymers of methacrylic acid esters, as well as mixtures thereof in 1 to 50% concentration.

To this base mass, may further be provided, for cosmetic, internal, that is to say pharmaceutical use, suitable inactive ingredients and carriers such as for example, additional skeleton formers which will be described in more detail hereinbelow, softening agents such as for example glycerol or sorbitan, fillers, such as lactose, dispersion materials such as disodium phosphate, pH adjusters, for example for disodium citrate, emulsifiers for example, lecithin, stabilizers such as ascorbic acid, co-solvents for example polyethylene glycol, natural colorants for example carotinoids, odorants or taste adjusters for example, fruit juice concentrates.

In a further embodiment of the process there may be added to the matrix softening agents in the range of 1 to 50% (relative to the mass to be worked) selected from the group consisting of glycerol, propylene glycol, polyethylene glycols, triacetin, sorbitol, sorbitan mixtures, sorbitol solutions, glucose syrup and other polyols suitably sugar alcohols, and mixtures thereof.

Furthermore, it is technologically advantageous to provide, in addition to the hydrophilic skeleton builders, other skeleton building substances to prescription mass.

As additional skeleton formers there may be added elastin hydrolysate, dextran, sugar for example saccharose, glycine, lactose, PVP (polyvinyl pyrrolidone) or combinations of the previously mentioned substances, in particular however? mannitol.

In considering plant extracts which are extremely thermolabile, the invention makes available in a further embodiment, surprisingly, molded parricles which have properties in accordance with the present invention which are formed solely under cold conditions. In this procedure, there is utilized a matrix of hydrophilic molecules selected from the group consisting of plant proteins, plant protein hydrolysates, elastin hydrolysate, collagen hydrolysate, cold water soluble gelatin, gelatin derivatives, and mixture of the above materials with a maximum molecular weight distribution of less than $10^5$D.

Particularly suitable softening agents are materials such as, for example, sorbitol which are solid after drying at room temperature. Surprisingly, after lyophilization, the matrix of such pellets gives rise to a solid or semi-solid structure which, after contact with aqueous media for example, under physiological conditions, has bioadhesive and high viscosity properties in the sense of the present invention.

In processing solid substances, these can either be dissolved in the fluid matrix mass or suspended therein (i.e, dry extracts).

In dealing with fluid, lipophilic extracts (fats or etheric oils) these are emulsified in the fluid matrix mass. Thus, the tenside properties of the matrix components, for example gelatin or collagen hydrolysate, can be utilized so that in many cases it is possible to operate without addition of an emulsifying agent. This is a substantial advantage for peroral preparations, as well as preparations to be used on sensitive or injured skin, as well as for cosmetic uses. Micro emulsions can be mixed with a matrix mass and similarly pelletized.

Fats or etheric oils, as well as simple or complex coaszervation spray dried encapsulated etheric oils, can be processed in the matrix mass of the present invention. Furthermore, microcapsules or coaszervates may be produced in the dissolved matrix mass, which then are formed into pellets together with the matrix mass and contain microcapsules in the matrix. Nano capsules may be similarly processed.

Furthermore, it may be desirable for cosmetic purposes to provide lipophilic components to the above described matrix mass, for example, phospholipids for the formation of lyposomes.

For cosmetic purposes, it may be desirable to add lipophilic components to the matrix mass, for example, phospholipids, for the formation of lyposomes.

In exceptional cases, the plant content materials themselves, in particular in the form of concentrates can serves as skeleton formers for the formation of pellets in accordance with the present invention.

It is clear that the mixtures of the present invention may be utilized for immediate processing in the fluid form of the process step of (A) above for the formation of containers, for example, molds, soft gelatin capsules, as well as other encapsulations.

In the procedural step described under (B) above, the above described matrix mass is provided into a dip bath in the range −108° C. to −210° C. for molding and shock freezing. As exceedingly cold and inert fluid, there is suitably used liquid nitrogen which does not alter the content of the pellets. In the deep cold fluid, there are formed rounded molded particles (pellets) which, after drying, comprise a mechanically stable matrix. The molding is achieved via a suitable dosing system. Each discrete drop takes, on either already during the free fall, or alternatively, in the bath as a result of the surrounding gas coating or surface tension system/gas, a spherical form before it freezes entirely. Just this rapid but nevertheless predictably controllable freezing fixes the condition of the system instantaneously, that is to say, none of the components of the plant extract can diffuse into the surrounding medium, dissolved components can no longer crystallize out, suspensions can no longer sediment, emulsions cannot break, thermally sensitive or moisture sensitive components of the plant juice are cryopreserved, the carrier skeleton cannot shrink further and so on. The production process with an inert fluid gas also has no negative impact and causes no change in the product. Of particular advantage is the preservation of desired properties. Furthermore, the process operates in the absence of solvent, has no negative environmental impact and can be carried out under sterile conditions.

As dosing system, there may be used all arrangements which produce discreet uniform drops of predetermined size, for example, pipette-type dropping arrangements, suitable spray or dispersion jets with dosage pumps. Furthermore, there may be utilized for the process of the present invention, dosage arrangements with single material jets which disperse the dropping materials in a timed or intermittent manner.

In a further desired embodiment of the present invention, there may be utilized the Cryopel$^R$ process developed by Messer Griesheim GmbH (based on DE OS 37 11 169). In combination with dip freeze arrangement, the Cryopel$^R$ arrangement is a particularly suitable apparative utilization of the process of the present invention on the industrial scale. This arrangement which can be driven by liquid nitrogen, is particularly advantageous economically. The apparatus is also suitable for sterile production. Continuous working procedures with minimal service and cleaning requirements makes possible the economic industrial scale utilization of the process of the present invention.

Figure 1:
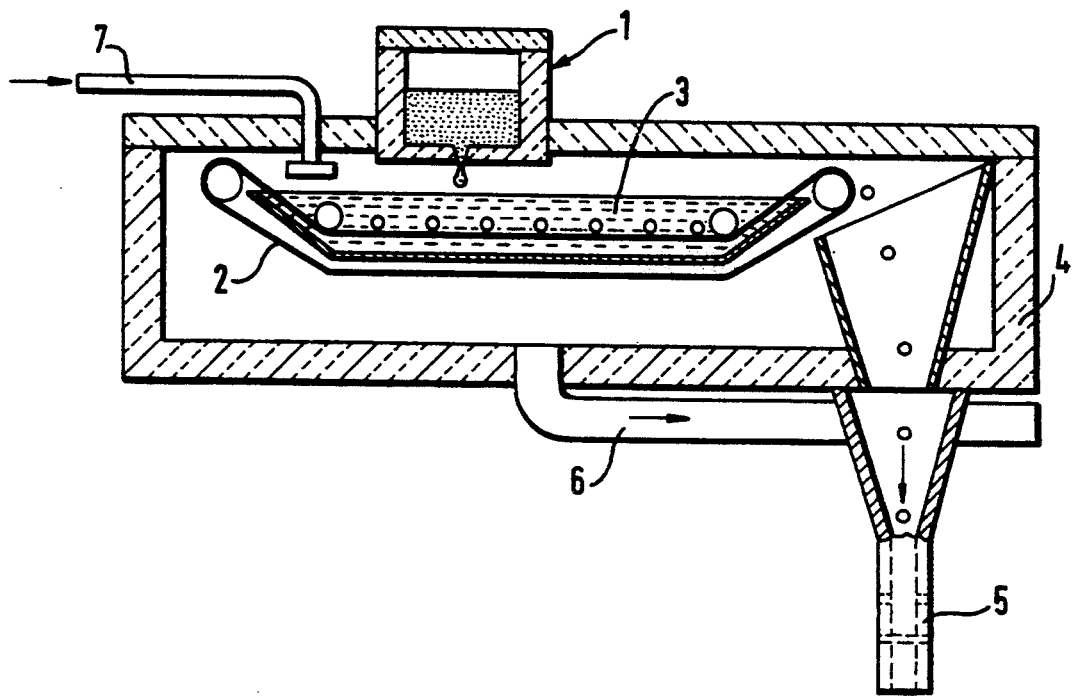
In FIG. 1 there is schematically illustrated the Cryopel$^R$ process developed by Messer Griesheim GmbH. The plant extract/matrix mass of the present invention is dropped from a heatable charge arrangement 1 over calibrated jets into the liquid nitrogen bath 3 at $-196°$ C. and formed under simultaneous shock freezing into round pellets. Via the continuously circulating transport band 24, the frozen product is removed via arrangement 5. The provision of the liquid nitrogen proceeds via line 7 and the thus generated nitrogen is removed via line 6. Insulation means 4 encompass the entire system.

If the system to be processed is not sufficiently fluid or capable of forming drops, it is possible, for example, to add between 1 to 10 wt % of water, the operating temperature could be raised or pressure can be utilized in the dosing step. In the contrary case (the system is of too low a viscosity), analogously reduced pressure may be utilized. In this manner, one achieves uniform formation as well as separation of individual drops.

The working temperature can be substantially varied. However, in the case of special plant extracts, for example aloe vera, it should be kept below 50° C. in order to avoid thermal impact upon the content of materials.

It is totally feasible to operate, with a Cryopel$^R$ dosage arrangement, masses whose viscosity vary over a wide range, for example, between $1 \times 10^{-3}$ to 10 to 12.5 pascal seconds, without any difficulty.

Further, exceedingly cold fluids which may be utilized in the present invention include, for example, inert gases, such as argon.

In dependence upon the chosen dosage system, it is possible to obtain a grain uniformity of over 70% which can additionally be improved by classification. The particles separated by classification can be recycled into the fluid state and again repelleted. Thus, there is provided a waste-free procedure.

In one embodiment of the above described process, the pellets can be dried, there being two modifications thereof.

Variant A

The pellets frozen at $-196°$ C. are transferred into a freeze drying arrangement. There are chosen temperatures of about 15° C. below the sublimation point of water at pressure of 0.1 Pa to 103 Pa (0.001 to 1.03 mbar). The drying arrangement which is carried out in a conventional freeze drying apparatus (condenser temperature—40° C.) at a temperature of 25° C. and 33 Pa (0.33 mBar) proceeds in the primary drying step in the sublimation of the water amorphously frozen in the shock freezing out of the matrix, the secondary drying (desorption) leads to an end product with a highly porous network. Such pellets are, compared to conventionally freeze dried products, particularly readily soluble and are preferred for the development of instant preparations.

Variant B

The frozen pellets are permitted to thaw and are conventionally dried. Here, it is advantageous for the acceleration of the drying process and the maintenance of a low temperature, to operate under vacuum, 3000 to 5000 Pa (30 to 50 mbar). Drying temperatures of up to 50° C. may be chosen, whereas the temperature of pellet matrix during the drying stage, because of the evaporation enthalpy of the fluid does not raise above 30° C.

For conventionally dried pellets (Variant B) it is necessary to utilize gel forming substances for the matrix which are capable of forming drops in sol form and, after cryopelletization and the melting of the gel, are stable after drying. The addition of softeners assists in the maintenance of uniformly round molded particles. The thus produced pellets show themselves to be economically formable and may be utilized both in cosmetic as well as pharmaceutical fields.

Compared to the known procedures of the art, the process of the present invention requires very little servicing and can be very economically carried out.

The pellets of the present invention are suitable for pharmaecutial purposes as well as for peroral and cosmetic purposes.

Pharmaceutical uses are for example:
Single dose peroral dosage form (pellets of 2 to 12 mm).
Pellets can be directly charged into hard gelatin capsules or into bags. 3)
As substrates for the formation of tablets, dragees, etc.
The pellets are exceedingly suitable for direct tableting. Because of the high readily attainable grain size predictability, no dosage problems arise.
Instant Teas filled into bags, the pellets can be utilized for the preparation of health care drinkable solutions (instant preparation). With the utilization of plant proteins, plant protein hydrolysates, collagen hydrolysates or gelatin with a maximum molecular weight distribution of from a few hundred D to less than 10⁻⁵D, the pellets of the present invention dissolve in water at ambient temperature in a few seconds. There are also possible mixtures of different plant extracts or with other active substances in this form.

Balneo therapeutics, inhalation materials which can be dissolved in hard water.

Formation of ointments, cremes, gels, for treatment of wounds for burns scrapes, etc.

Formation of plasters for wounds and wound powders.

Sterile active material pellets as wound inserts.

As cosmetic uses there may be mentioned for example:

Formation of cremes, instant cremes, moisturizing emulsions, sun protection substances, substances against sunburn, shampoos, toothpaste, soaps, bath additives, and facial waters.

Direct use of the pellets for the preparation of face masks, powders, and the like.

Use in cosmetics in dissolved or semi-solid form.

Use in cosmetics in combination with other active substances.

Because of the considerable variability of the prescription masses and the described formation procedures, the properties of the pellets of the present invention can be very readily provided for the desired utilization purpose.

Special matrix formation enables the direct utilization of pellets in solid or half-solid forms whereby the solution results during dosing.

By variation of the bloom level of the gelatin used in the present invention, only the properties, as for example the control of the solution speed of the pellets of the present invention, but also the desired viscosity of the thus produced aqueous solution, can be directed in accordance with the ultimate use.

Such pellets have a plurality of advantages: With respect to the conventionally produced liquid or dry extracts, the plant content material remains substantially unaltered in preservative-free form.

Where there are added softening agents, they retain an unalterable appearance and additionally, are very pleasant to ingest. Undesirable taste is already covered up by the matrix materials themselves. They make possible an alcohol free dosage form for plant extracts or they can be utilized as a homeopathic globulai. In contrast to soft gelatin capsules, there is no possibility of leakage of the active material. Labile etheric oil are brought into as solid form. In contrast to conventional commercially available solutions and tinctures, they have a low weight and are very readily swollowable in single unit dosage forms.

The invention is described in greater detail in the following examples.

EXAMPLE 1

Pellets as bath additive for a medicinal bath utilizable for rheumatic complaints (pharmaceutical use).
2.5 kg. gelatin (150 bloom)
1.0 kg. glycerin
6.5 kg. water
375 g. of Juniper berry oil (etheric oil)

The gelatin is preswollen with glycerin/water/mixture at room temperature for 30 minutes and then dissolved at 60° C. After addition of the etheric oil of Juniper berries, the mixture is homogenized with an Ultra-Turrax homogenizer and the thus obtained emulsion dropped into liquid nitrogen at a temperature of −196° C. via the dosage arrangement illustrated in FIG. 2. The thus produced pellets are dried at 20° C. for 24 hours in air and charged to containers.

20 g. of these pellets are utilized as an additive for a full bathtub and dissolve completely in the warm water, releasing the etheric oil. There is thus provided a medicinal bath utilizable in rheumatic complaints.

As an advantageous treatment for muscle pains, there may be utilized a mixture of 10 g. of these pellets with 10 g. of similarly produced rosemarin oil pellets.

For the formation of a soothing bath lemon balm oil can be utilized.

For the formation of inhalation pellets, there may be utilized oleum pini pumilionis and the pellets dissolved in hot water before inhalation.

EXAMPLE 2

Vitamin E emulsion pellets freeze-dried for utilization in a protective creme (cosmetic use).
0.15 kg. Vitamin E derived from wheat germ oil.
1.0 kg. collagen hydrolysate, molecular weight 13,000 to 18,000 g/ml.
9 kg. water.

Collagen hydrolysate is dissolved in water and liquid Vitamin E added under homogenization with an Ultra-Turrex homogenizer. The thus produced emulsion is dropped to liquid nitrogen via the dosage arrangement of FIG. 2 and thus shock-frozen. Thereafter, the water is removed from the pellets by freeze drying.

The dried pellets can then be compounded as "solid" Vitamin E in a protective creme in the following manner.

Oily Phase:
Tegomuls$^R$ 90S—2.5 kg.
Soya Bean Oil—5.0 kg.
Cocoa Butter—1.5 kg.
Cetyl alcohol—1.5 kg.

Aqueous Phase:
Distilled Water—3.0 kg.

Active Substance:
(corresponding to 230 g. Vitamin E emulsion pellets).
Vitamin E—30 g.

The pellets are emulsified in 1.8 l. of water.

The components of the oily phase are melted at 65° C. and 1.2 kg. of water warmed to that temperature is added thereto and homogenized under stirring. After cooling of the creme to 30° C., the Vitamin E collagen hydrolysate emulsion is stirred in.

EXAMPLE 3

Echinacea Pellets, Dosage Form
Echinacea proto tincture—2.16 kg.
Collagen hydrolysate, mean molecular weight, 3,000 g/ml.—0.5 kg.
Distilled water—0.5 kg.

The collagen hydrolysate is dissolved in water at room temperature and mixed with the proto tincture. The ethanol is removed from the ethanol/water mixture at 40° C. under a vacuum of 5,000 Pa (50 mbar) in a single step vacuum evaporator.

Figure 2:
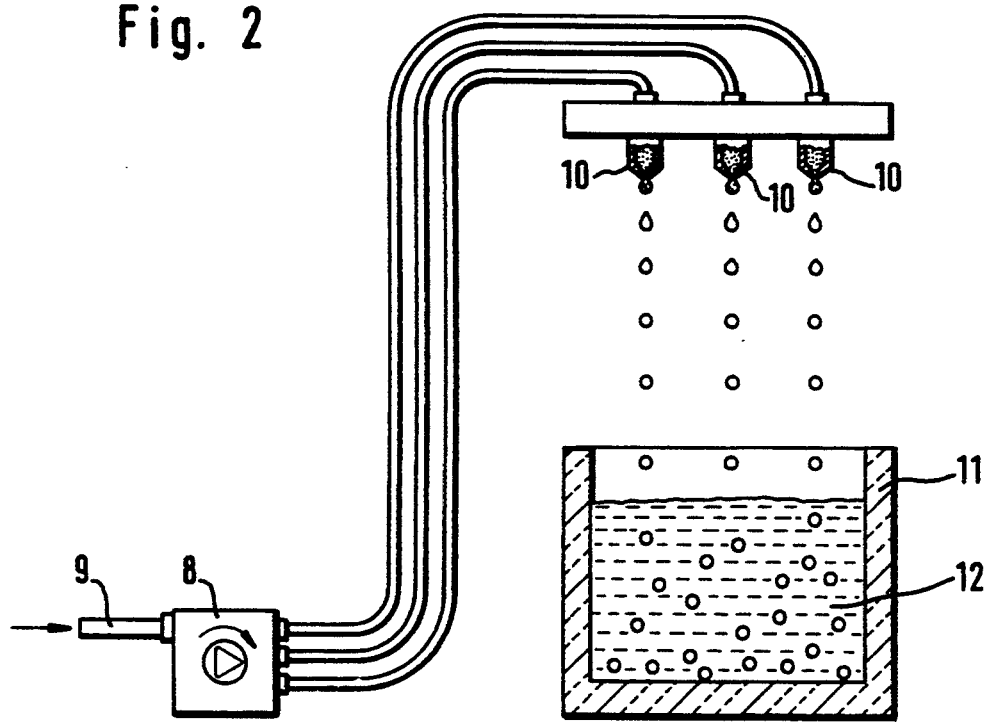
FIG. 2 is a schematic representation of the process in which a regulatable dosage pump 8 continually drops the plant extract/matrix mass at a temperature from between room temperature to a maximum of 50° via line 9, continuously through the heatable drop jets 10 into the insulation bath 11, comprising the liquid nitrogen 12. The shock frozen pellets are removed batchwise. This arrangement permits the processing of highly viscous masses.

The echinacea containing the solution is dropped into liquid nitrogen at −196° C. via the apparatus of FIG. 2 to thus form the pellets. These are subjected to a primary drying at −50° C. and 5 Pa (0.05 mbar) and a secondary drying at 22° C.

After drying, the echinacea pellets have a diameter of 5 mm. The consumption of 3×1 pellet a day corresponds to the dosage of the peophylactic material against colds.

EXAMPLE 4

Echinacea Soft Gelatin Pellets
Gelatin (140 bloom)—250 g.
Glycerin—100 g.
Echinacea fresh plant juice (press juice)—5,000 g.

Gelatin is swollen in a mixture of fresh plant juice and glycerin for 30 minutes then warmed at 40° C. Thereafter, as much water is removed in a single step evaporator at 40° C. under a vacuum of 5,000 Pa (50 mBar) as would still enable the mass to flow freely. This mass is then cryopelletted via the dosage arrangement of FIG. 2 in Example 1 and dried under the same conditions. The pellets have a diameter of 3.5 mm. and are filled into a dosage metering device. For prophylactic purposes there is taken 5 pellets per single dose.

EXAMPLE 5

Rutin Suspension
Gelatin (140 bloom)—200 g.
Glycerin—150 g.
Distilled Water—650 g.
Rutin—87.5 g.

Gelatin, glycerin, and water are formed into a solution in accordance with Example 1. Rutin is suspended therein in powder form. As is set forth in Example 1, the mixture pelleted and dried. The pellets have a diameter of 3.5 mm and 5 pellets comprise a single dose of 50 mg. of Rutin.

We claim:

1. Plant extract containing dried cryopellets comprising a plant extract the activity and amount whereof is essentially undiminished by the cryopelleting dispersed in a matrix at least 50% w/w whereof comprising substantially of skeleton forming water soluble hydrophilic macromolecular material selected from the group consisting of collagen, scleroproteins, gelatin, fractionated gelatin, collagen hydrolysates, succinylated gelatin, elastin hydrolysates, plant proteins, plant protein hydrolysates and mixtures thereof.

2. Dried cryopellets in accordance with claim 1 further comprising at least one additional skeleton forming hydrophilic material selected from the group consisting of albumins, plant proteins, plant protein hydrolysates, agar agar, gum arabic, pectins, tragacanth, xanthane, natural and modified starches, dextrans, dextrines, maltodextrin, chitosan, alginates, cellulose derivatives, dextran, sugar, glycine, lactose, mannitol and polyvinylpyrrolidone.

3. Dried cryopellets in accordance with claim 1 additionally comprising pharmaceutically acceptable inactive ingredients or carrier material in the matrix.

4. Dried cryopellets in accordance with claim 1 having a content of plant extract of 0.1 to 98 wt. % (calculated as a dry substance).

5. Dried cryopellets in accordance with claim 1 wherein said plant extract is selected from the group consisting of solid plant extracts, liquid plant extracts, hydrophilic plant extracts, lipophilic plant extracts, individual plant content materials as well as mixtures thereof.

6. Dried cryopellets in accordance with claim 1 existing as lyophilisates.

7. Dried cryopellets in accordance with claim 1 which are rapidly dissolvable in aqueous media wherein said matrix comprises substantially a plant protein, plant protein hydrolysate, collagen hydrolysate, cold water soluble gelatin derivative or gelatin the major portion whereof having a molecular weight under $10^5 D$.

8. Dried cryopellets in accordance with claim 1 wherein said matrix comprises as softeners, glycerin or sorbitol of between 1 and 50 wt. %, relative to the total mass of said pellets.

9. Dried cryopellets in accordance with claim 8 existing in solid or semisolid form.

10. Dried cryopellets in accordance with claim 8 comprising, as a sol/gel former, a gelatin the major portion whereof having a molecular weight above $10^5 D$.

11. Process for the preparation of a plant extract containing dried cryopellet having a matrix, the amount and activity of said extract being essentially undiminished by the cryopelleting, comprising the steps of:

a) mixing said extract with which is selected from the group consisting of hydrophilic fluid plant extracts, aqueous extracts, alcoholic extracts, as well as mixtures thereof a skeleton forming water soluble hydrophilic macromolecular material selected from the group consisting of collagen, gelatin, fractionated gelatin, collagen hydrolysate, succinylated gelatin, plant proteins, plant protein hydrolysates, elastin hydrolysates as well as mixtures thereof, said material comprising at least 50% by weight of said mixture;

b) dropping the thus obtained mixture into an exceedingly cold inert fluid having a density less than that of the mixture of (a) at a temperature of between −70° and −270° C. whereby the cryopellets are molded; and c) drying said cryopellets.

12. Process according to claim 11 wherein in step a) an aqueous solution of said macromolecular material is made and mixed with said hydrophilic fluid plant extract.

13. Process according to claim 11 wherein where the plant extract is an alcoholic extract, the said process comprising a final step c), wherein said alcoholic solvent is removed.

14. Process according to claim 11 wherein after step a) and prior to step b), the solution is concentrated.

15. Process according to claim 11 wherein where the extract is a lipophilic extract, it is emulsified into the matrix mass in step a).

16. Process according to claim 11 wherein in step a) a solid plant extract is dissolved into said macromolecular material.

17. Process according to claim 11 wherein in step a) a solid plant extract is suspended in said macromolecular material.

18. Process according to claim 11 wherein the mixture is dropped into liquid nitrogen.

19. Process according to claim 11 wherein said drops are of equal predetermined form and are created by means of a dosing system capable of creating same.

20. Process according to claim 11 comprising of freeze drying the thus dried cryopellets.

21. Process according to claim 11 wherein, to the product of step a) there is added at least one additional skeleton forming hydrophilic material selected from the group consisting albumin, agar agar, gum arabic, pectins, tragacanth, xanthane, natural and modified starches, dextranes, dextrines, maltodextrin, chitosan, alginates, cellulose derivatives, dextran, sugar, glycine, lactose, mannitol, and polyvinylpyrrolidone.

22. Process according to claim 11 comprising the further step of adding to the mixture of step a) as softeners, glycerin, sorbitol or mixtures thereof comprising 1 to 50 wt. % relative to the entire mass of extract and skeleton former.

23. Process according to claim 11 comprising the additional step wherein the cryopellets are dried at a maximum of 50° C.

24. Process according to claim 11 wherein, as macromolecular material, gelatins the major portion whereof having a molecular weight above $10^5 D$ are mixed with the plant extract at a maximum temperature of 60° C.

25. A pharmaceutical preparation containing the dried cryopellets of claim 1.

26. A food preparation for health care containing the dried cryopellets of claim 1.

27. A cosmetic preparation containing the dried cryopellets of claim 1.

28. Dried cryopellets in accordance with claim 9 comprising, as a sol/gel former, a gelatin having a maximum molecular weight distribution above $10^5 D$.

* * * * *